United States Patent
Kuechler et al.

[11] Patent Number: 6,121,504
[45] Date of Patent: Sep. 19, 2000

[54] PROCESS FOR CONVERTING OXYGENATES TO OLEFINS WITH DIRECT PRODUCT QUENCHING FOR HEAT RECOVERY

[75] Inventors: Keith H. Kuechler, Friendswood; James R. Lattner, Seabrook, both of Tex.

[73] Assignee: Exxon Chemical Patents Inc., Houston, Tex.

[21] Appl. No.: 09/069,403

[22] Filed: Apr. 29, 1998

[51] Int. Cl.[7] .................................................. C07C 1/00
[52] U.S. Cl. ........................ 585/640; 585/638; 585/639; 585/910
[58] Field of Search .................... 585/640, 639, 585/638, 910

[56] References Cited

U.S. PATENT DOCUMENTS

| | | | |
|---|---|---|---|
| 2,949,493 | 10/1960 | Happel et al. | 585/640 |
| 4,044,061 | 8/1977 | Chang et al. | 260/668 R |
| 4,387,263 | 6/1983 | Vogt et al. | 585/640 |
| 4,440,871 | 4/1984 | Lok et al. | 502/214 |
| 4,499,327 | 2/1985 | Kaiser | 585/640 |
| 4,567,029 | 1/1986 | Wilson et al. | 423/306 |
| 4,579,999 | 4/1986 | Gould et al. | 585/640 |
| 4,861,743 | 8/1989 | Flank et al. | 502/214 |
| 4,861,938 | 8/1989 | Lewis et al. | 585/640 |
| 4,929,780 | 5/1990 | Wright et al. | 585/303 |
| 5,095,163 | 3/1992 | Barger | 585/640 |
| 5,126,308 | 6/1992 | Barger et al. | 502/214 |
| 5,157,181 | 10/1992 | Stine et al. | 585/329 |
| 5,191,141 | 3/1993 | Barger et al. | 585/640 |
| 5,714,662 | 2/1998 | Vora et al. | 585/640 |
| 5,744,680 | 4/1998 | Mulvaney, III et al. | 585/640 |

FOREIGN PATENT DOCUMENTS

WO 93/24431 12/1993 WIPO.
WO 96/28408 9/1996 WIPO.

OTHER PUBLICATIONS

Chang, "Methanol Conversion to Light Olefins," *Catal. Rev.–Sci. Eng.*, 26(3&4), pp. 323–345 (1984).
Kaeding, et al., "Production of Chemicals from Methanol," *Jounal of Catalysts*, vol. 64, pp. 155–64 (1980).
J. Chen et al., Studies in Surface Sciences and Catalysts, Proceedings of the Tenth International Catalysis Society, vol. 84, pp. 17–31 (1994).

*Primary Examiner*—Hien Tran
*Assistant Examiner*—Thuan D. Dang
*Attorney, Agent, or Firm*—Bradley A. Keller

[57] ABSTRACT

The present invention relates to a process for catalytically converting a feedstock comprising an oxygenates to olefins with direct product quenching to increase heat recovery and to improve heat integration.

27 Claims, 1 Drawing Sheet

PROCESS FOR CONVERTING OXYGENATES TO OLEFINS WITH DIRECT PRODUCT QUENCHING FOR HEAT RECOVERY

FIELD OF THE INVENTION

The present invention relates to a process for increasing the efficiency of heat recovery and improving heat integration with direct product quenching in the selective conversion of oxygenates to olefins.

BACKGROUND OF THE INVENTION

Light olefins (defined herein as ethylene, propylene, butenes and mixtures thereof) serve as feeds for the production of numerous important chemicals and polymers. Light olefins traditionally are produced by cracking petroleum feeds. Because of the limited supply and escalating cost of petroleum feeds, the cost of producing olefins from petroleum sources has increased steadily. Efforts to develop and improve olefin production technologies, particularly light olefins production technologies, based on alternative feedstocks have increased.

An important type of alternative feedstocks for the production of light olefins are oxygenates, such as alcohols, particularly methanol and ethanol, dimethyl ether, methyl ethyl ether, methyl formate, and dimethyl carbonate. Alcohols may be produced by fermentation, or from synthesis gas derived from natural gas, petroleum liquids, carbonaceous materials including coal, recycled plastics, municipal wastes, agricultural products, or most organic materials. Because of the wide variety of raw material sources, alcohol, alcohol derivatives, and other oxygenates have promise as an economical, non-petroleum feedstock source for olefin production.

The conversion of oxygenates to olefins takes place at a relatively high temperature, generally higher than about 250° C., preferably higher than about 300° C. Because the conversion reaction is exothermic, the effluent typically has a higher temperature than the initial temperature in the reactor. Many methods and/or process schemes have been proposed to manage the heat of reaction generated from the oxygenate conversion reaction inside of the reactor in order to avoid temperature surges and hot spots, and thereby to reduce the rate of catalyst deactivation and reduce the production of undesirable products, such as methane, ethane, carbon monoxide and carbonaceous deposits or coke. It would be very useful to have a process that effectively utilizes the heat of reaction contained in the products exiting the oxygenate conversion reactor, optimizes heat recovery, and reduces overall utility consumption in the conversion of oxygenates to olefins. Such a process is environmentally, economically, and commercially more attractive.

SUMMARY OF THE INVENTION

The present invention provides a process for converting an oxygenate to olefins with increased heat recovery and heat integration, said process comprising: heating a feedstock comprising said oxygenate having a first heat content from a first temperature to a second temperature through from one to about three stages having successively higher heat contents; contacting said feedstock at said second temperature with a catalyst comprising a molecular sieve under conditions effective to produce a deactivated catalyst having carbonaceous deposits and a product comprising said olefins, wherein said molecular sieve comprises pores having a diameter smaller than about 10 Angstroms and said product has a third temperature which is higher than said second temperature; quenching said product with a medium at an initial temperature and in an amount sufficient for forming a light product fraction and a heavy product fraction wherein said light product fraction comprises light olefins and said heavy product fraction has a final temperature which is higher than said first temperature by at least about 5° C.; using said heavy product fraction to provide heat at one or more of said stages to achieve said higher heat contents.

DETAILED DESCRIPTION OF THE INVENTION

Figure 1:
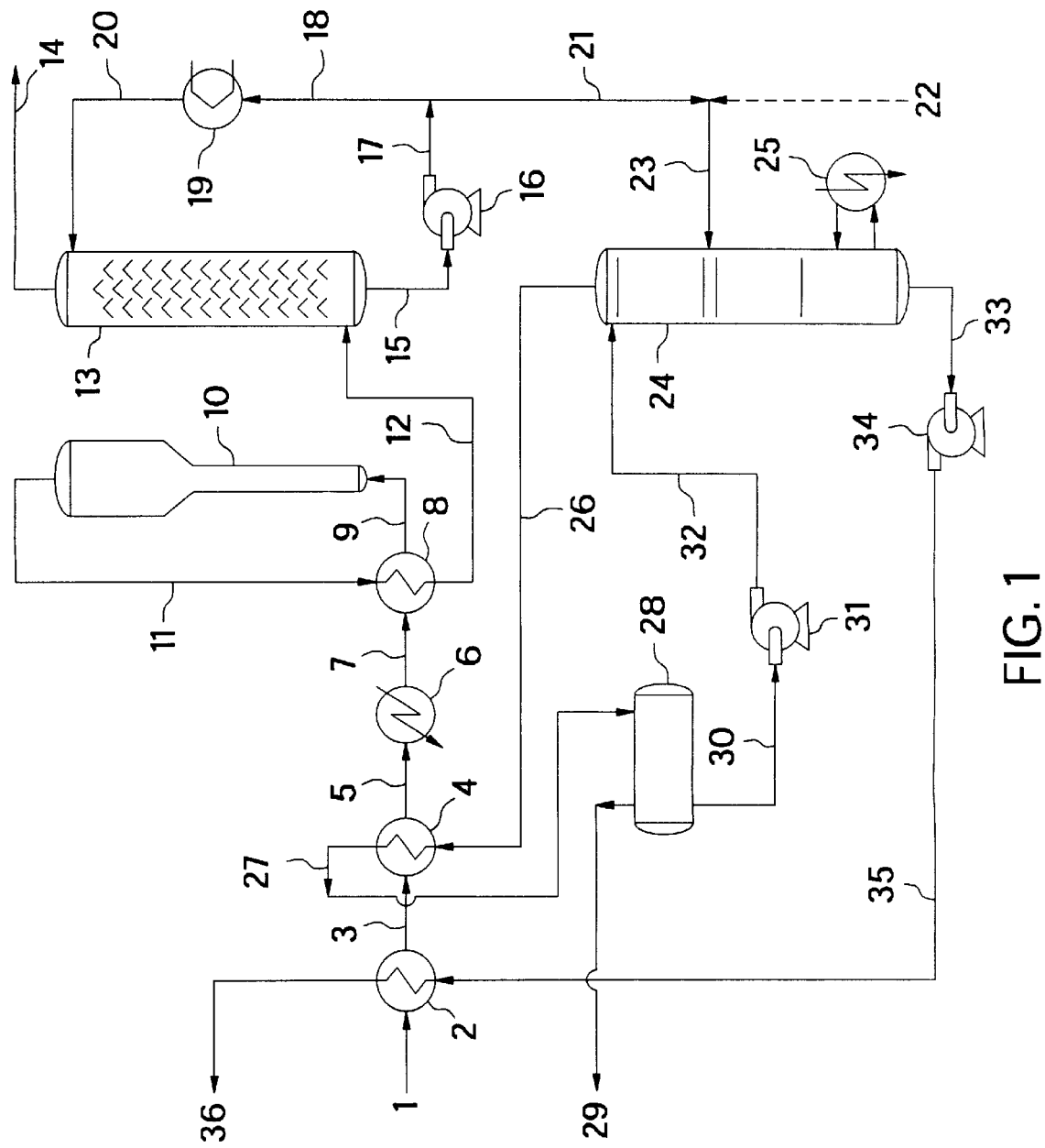
FIG. 1 is a flow diagram of a preferred embodiment of increasing heat recovery in the present invention.

The present invention provides a process for increasing heat recovery and decreasing energy and utility requirements during the conversion of oxygenates to olefins. The process involves taking the product mixture, including any unreacted oxygenate feed, from an oxygenate conversion reactor and, without fractionating the products, directly quenching the product mixture with a suitable medium, preferably water. This type of quenching hereinafter will be referred to as "direct product quench." The direct product quench removes heat from the product mixture, causing higher boiling components, such as water and unreacted oxygenate feed, to condense and form a heavy product fraction. The heavy product fraction is separated from the light product fraction comprising gaseous hydrocarbon components such as light olefins, methane, ethane, propane, and butanes. The heavy product fraction may be divided further into several fractions. The heavy production fraction, or any, or all of the several fractions may be subjected to various techniques or methods to separate the quench medium from other components. The heavy product fraction, or any, or all of the several fractions or streams produced from quench medium separations thereof, may be used to supply at least part of the heat needed to vaporize or otherwise to increase the heat content of the oxygenate feedstock, through from one to about three stages, prior to being introduced into the oxygenate conversion reactor for contacting the oxygenate conversion catalyst. These stages give the oxygenate feedstock successively higher heat content.

Most catalysts that are used in oxygenate conversion processes comprise molecular sieves, both zeolitic (zeolites) and non-zeolitic types. The present invention should achieve many of the desired improvements using substantially any molecular sieve catalyst, regardless of the structure type or pore size. Mixtures of zeolitic and non-zeolitic molecular sieves also may be used. Preferred molecular sieve catalysts for use according to the present invention comprise "small" and "medium" pore molecular sieve catalysts. "Small pore" molecular sieve catalysts are defined as catalysts with pores having a diameter of less than about 5.0 Angstroms. "Medium pore" molecular sieve catalysts are defined as catalysts with pores having a diameter in the range of from about 5.0 to about 10.0 Angstroms. "Large pore" molecular sieve catalysts are catalysts with pores having a diameter larger than about 10.0 Angstroms. Generally, large pore molecular sieve catalysts, without additional appropriate modifications and/or treatments, are not preferred catalysts for converting oxygenates to light olefins.

Zeolitic molecular sieve catalysts suitable for the use in the present invention with varying degree of effectiveness include, but are not necessarily limited to AEI, AFI, CHA, ERI, LOV, RHO, THO, MFI, FER, and substituted examples of these structural types, as described in W. M. Meier and D. H. Olson, *Atlas of Zeolitic Structural Types* (Butterworth Heineman-third edition, 1997), incorporated herein by reference. Preferred zeolite catalysts include but are not necessarily limited to zeolite 3A, zeolite 4A, zeolite 5A (collectively referred to hereinafter as zeolite A), ZK-5, ZSM-5, ZSM-34, erionite, chabazite, offretite, silicalite, borosilicates and mixtures thereof. See Meier and Olson. These zeolites may be obtained from many companies and commercial sources such as Mobil, AMOCO, UCI, Engelhard, Aldrich Chemical Company, Johnson Matthey Company, Union Carbide Corporation, and others.

Silicoaluminophosphates ("SAPO's") are one group of non-zeolitic molecular sieves that are useful in the present invention. Suitable SAPO's for use in the invention include, but are not necessarily limited to SAPO-17, SAPO-18, SAPO-34, SAPO-44, and mixtures thereof. Small pore SAPO's are preferred for producing light olefins. A preferred SAPO is SAPO-34, which may be synthesized according to U.S. Pat. No. 4,440,871, incorporated herein by reference, and Zeolites, Vol. 17, pp. 212–222 (1996), incorporated herein by reference. SAPO-18 may be synthesized according to J. Chen et al. *Studies in Surface Sciences and Catalysis*, Proceedings of the Tenth International Catalysis Society, Volume 84, pp 17–31 (1994).

Substituted silicoaluminophosphates (substituted SAPO's) form another class of non-zeolitic molecular sieves known as "MeAPSO's," that are suitable for use as catalysts in the present invention. MeAPSO's are described in U.S. Pat. No. 4,567,029 and U.S. Pat. No. 5,126,308, incorporated herein by reference. SAPO's with substituents incorporated after synthesis, also may be suitable for use in the present invention. Suitable substituents, "Me," include, but are not necessarily limited to nickel, cobalt, manganese, chromium, iron, zinc, strontium, magnesium, barium, and calcium. Preferred MeAPSO's include, but are not necessarily limited to NiSAPO-17, NiSAPO-34, Co-SAPO-17, Co-SAPO-34, Sr modified SAPO-17 (SrAPSO-17), Sr modified SAPO-18 (SrAPSO-18), Sr modified SAPO-34 (SrAPSO-34), SrAPSO-44, and mixtures thereof. Different substituents may be incorporated during or after the synthesis of the silicoaluminophosphates.

Substituted aluminophosphates (ALPO) known as MeAPO's may also be used as the non-zeolitic molecular sieve catalysts for the present invention. MeAPO's include, but are not necessarily limited to ZnAPO, ZrAPO, TiAPO, and mixtures thereof. These molecular sieves may be synthesized according to U.S. Pat. No. 4,861,743, U.S. Pat. No. 4,567,029, and U.S. Pat. No. 5,126,308.

Because the catalyst may be used in a variety of oxygenate conversion reactors and/or under a variety of reaction conditions, it may contain binders, fillers, or other material to provide better catalytic performance, attrition resistance, regenerability, and other desired properties for a particular type reactor. When used in a fluidized bed reactor, the catalyst should be fluidizable under the reaction conditions. A catalyst may be subjected further to a variety of treatments to achieve the desired physical, mechanical, and catalytic characteristics. Such treatments include, but are not necessarily limited to calcination, milling, ball milling, grinding, spray drying, hydrothermal treatment with steam at elevated temperatures—from about 400° C. to about 800° C., acid treatment, base treatment, and combinations thereof.

The process for converting oxygenates to olefins employs an organic starting material—a feedstock—preferably comprising "oxygenates." As used herein, the term "oxygenates" is defined to include, but not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety preferably should contain in the range of from about 1–10 carbon atoms and more preferably in the range of from about 1–4 carbon atoms. Representative oxygenates include, but are not necessarily limited to, lower straight chain or branched aliphatic alcohols, their unsaturated counterparts, and their nitrogen, halogen and sulfur analogues. Examples of suitable compounds include, but are not necessarily limited to: methanol; ethanol; n-propanol; isopropanol; $C_4$–$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; methyl formate, methyl acetate, formaldehyde; di-methyl carbonate; trimethyl orthoformate, dimethyl ketone; n-alkyl amines, n-alkyl halides, n-alkyl sulfides having n-alkyl groups of comprising the range of from about 3 to about 10 carbon atoms; and mixtures thereof. Preferred oxygenate feedstocks include, but are not necessarily limited to methanol, dimethyl ether, dimethyl carbonate, methyl formate, and mixtures thereof. As used herein, the term "oxygenate" designates only the organic material used as the feed. The total charge of feed to the reaction zone may contain additional compounds such as diluents.

Preferably, the oxygenate feedstock should be at least partially vaporized and contacted in a suitable oxygenate conversion reactor with the selected molecular sieve catalyst under process conditions effective to produce the desired olefins at an acceptable conversion level with desired selectivities.

The temperature employed in the conversion process may vary over a wide range depending, at least in part, on the pressure, the selected catalyst, the reactor configuration, the weight hourly space velocity, and other reaction parameters. Although not limited to a particular temperature, best results will be obtained if the process is conducted at temperatures in the range of from about 200° C. to about 750° C., preferably in the range of from about 250° C. to about 650° C., and most preferably in the range of from about 300° C. to about 600° C.

Since the oxygenate feedstock normally is stored at ambient temperatures before it is used in the conversion process, the feedstock has to be heated to a higher temperature with a much higher heat content suitable for contacting the oxygenate conversion catalyst. It is preferable to increase the heat content and/or the temperature of the feedstock through from one to about three intermediate stages, with each stage having a successively higher heat content. Many different streams in the oxygenate conversion process may be suitable sources for providing the necessary heat to increase heat contents. These streams, including those derived from the heavy product fraction from the quench tower and the streams from the fractionator separating quench medium from other components, are described in more detail below. It should be pointed out that a stream may have a higher heat content after a heat exchange even though it has a lower temperature, primarily resulting from pressure changes and/or phase changes, such as vaporization of a liquid. The pressure and/or phase changes are needed for the oxygenate conversion process.

Light olefin products will form—although not necessarily in optimum amounts—at a wide range of pressures, including but not necessarily limited to sub- and super-atmospheric pressures and autogeneous pressures,—in the range of from about 1 kPa to about 100 MPa. A preferred pressure is in the range of from about 5 kPa to about 50 MPa, most preferably in the range of from about 50 kPa to about 500 kPa. The foregoing pressures are exclusive of diluent, if any is present, and refer to the partial pressure of the feedstock as it relates to oxygenate compounds and/or mixtures thereof. Pressures outside of the stated ranges may be used and are not excluded from the scope of the invention.

A steady state or semi-steady state production of light olefin products may be attained and/or sustained over a period of time, largely determined by the reactor type, the reactor configuration, the temperature, the pressure, the catalyst selected, the amount of spent catalyst recirculated (if any), the level of catalyst regeneration, the amount of carbonaceous materials left on the regenerated or partially regenerated catalyst, the weight hourly space velocity (WHSV), the amount of quench medium used, and other relevant process design characteristics.

A wide range of WHSV, defined as weight of total oxygenate feedstock per hour per weight of catalyst, for the feedstock will function in the present invention. Depending on the reactor type, the desired conversion level, the feedstock composition, and other reaction parameters, the WHSV generally should be in the range of from about 0.01 $hr^{-1}$ to about 1000 $hr^{-1}$, preferably in the range of from about 0.1 $hr^{-1}$ to about 500 $hr^{-1}$, and most preferably in the range of from about 0.5 $hr^{-1}$ to about 200 $hr^{-1}$. Since the catalyst may contain other materials which act as inerts, fillers, or binders; the WHSV is calculated only on the weight basis of oxygenate and molecular sieve part of the catalyst.

One or more diluents may be fed to the reaction zone with the oxygenates, such that the total feed mixture comprises diluent in a range of from about 1 mol % and about 99 mol %. Diluents which may be employed in the process include, but are not necessarily limited to, helium, argon, nitrogen, carbon monoxide, carbon dioxide, hydrogen, water, paraffins, other saturated hydrocarbons (such as methane, ethane, propane, and mixtures thereof), aromatic compounds, and mixtures thereof. Preferred diluents include, but are not necessarily limited to water and nitrogen.

Oxygenate conversion should be maintained sufficiently high to avoid the need for commercially unacceptable levels of recycling. 100% oxygenate conversion is preferred for the purpose of avoiding feedstock recycle completely. However, a reduction in unwanted by-products is observed frequently when the oxygenate, particularly methanol, conversion level is about 98% or less. Accordingly, there is usually from about 0.05 mol % to about 50 mol % unreacted oxygenate in the product stream along with the oxygenate conversion products comprising olefins, water, and/or other byproducts. It is preferable to recover as much of the unreacted oxygenate as possible for recycle purposes. In any event, the oxygenate content in waste water may need to be reduced to an environmentally acceptable level before byproduct water can be discharged.

Therefore, it is desirable to consider this incomplete oxygenate conversion in the overall heat recovery and heat integration scheme, i.e. optimizing heat recovery and heat integration, when using a fractionator to recover unreacted oxygenates. If the oxygenate conversion level is high enough and/or recovery of unreacted oxygenate is not warranted for economic or environmental purposes, then this invention calls for utilizing heat directly from the heavy product fraction or any or all of the several fractions into which the heavy product fraction may be divided.

After contacting the oxygenate feed, the catalyst becomes fully or partially deactivated due to accumulation of carbonaceous deposits (also called coke) on the catalyst surface and/or inside the pores. Fully deactivated catalyst The deactivated catalyst having carbonaceous deposits is separated from the other oxygenate conversion products. Preferably at least a portion of the deactivated catalyst is separated and withdrawn from the oxygenate conversion reactor intermittently, semi-continuously, continuously, or in batch. Before the deactivated catalyst is recycled back to the oxygenate conversion and used again, a suitable regeneration is carried out on at least a portion of the withdrawn deactivated catalyst to remove at least a portion of the carbonaceous deposits, in the range of from about 0.1 wt % to about 99.9 wt %, preferably at least about 1.0 wt % of the carbonaceous deposits should be removed. Complete regeneration—removing 100 wt % of the original carbonaceous deposits on all of the deactivated catalyst—also may be carried out, but it is found that complete regeneration has a tendency of leading to production of large amounts of undesirable byproducts such as methane and/or hydrogen.

Preferably, the regeneration is carried out in the presence of a gas comprising oxygen or other oxidants. Air and air diluted with nitrogen, steam, and/or $CO_2$ are preferred regeneration gases. The catalyst regeneration temperature should be in the range of from about 250° C. to about 750° C., preferably from about 300° C. to about 700° C.

Almost any type of reactor will provide some conversions of the oxygenates to olefins. Reactor type includes, but is not necessarily limited to fluidized bed reactor, riser reactor, moving bed reactor, fixed bed reactor, continuously stirred tank reactor, hybrids and combinations thereof. Increased heat recovery and improved heat integration in the present invention can be achieved with most any reactor types. A preferred reactor system for the present invention is a circulating fluid bed reactor with continuous or semi-continuous catalyst regeneration, similar to a modern fluid catalytic cracker. Fixed beds may be used, but are not preferred.

Because the oxygenate conversion reaction is highly exothermic, the oxygenate conversion reaction product effluent generally has a higher temperature than the feedstock temperature just before contacting the catalyst. In one embodiment of the present invention, the feedstock from the storage tank at a first temperature and having a first heat content is heated through several intermediate stages in heat exchangers to a second desired temperature prior to contacting the oxygenate conversion catalyst. It is preferable to have from one to about three stages of heat exchange to provide streams with successively higher heat contents. Various streams from the oxygenate conversion process at different temperatures and external sources of heat, such as that from steam, may be used as heat exchanger fluids to increase either the heat content, the temperature, or both, of the feedstock oxygenate.

After contacting the oxygenate feedstock with the oxygenate conversion catalyst, the oxygenate conversion reaction product effluent comprising olefin products is quenched directly by contacting a suitable quench medium in a quench tower without first going through a product fractionation step. Alternatively, the product effluent may be used to provide heat directly to the oxygenate feedstock. The temperature and the heat content of the product effluent are reduced to intermediate levels afterwards. The product effluent at this lower temperature and lower heat content is sent to the quench tower for direct quenching.

The compounds in the effluent stream which are gaseous under the quenching conditions are separated from the quench tower as a light product fraction for olefin product recovery and purification. The light product fraction comprises light olefins, dimethyl ether, methane, CO, $CO_2$, ethane, propane, and other minor components such as water and unreacted oxygenate feedstock. The compounds in the effluent stream which are liquid under quenching conditions, are separated from the quench tower as a heavy product fraction for heat recovery, and possible division into several fractions and separation of the quench medium. The heavy product fraction comprises byproduct water, a portion of the unreacted oxygenate feedstock (except those oxygenates that are gases under quenching conditions), a small portion of the oxygenate conversion byproducts, particularly heavy hydrocarbons (C5+), and usually the bulk of the quench medium.

Preferably, a quench medium is selected from a composition which remains substantially as a liquid under the quenching conditions, thus minimizing the amount of the quench medium present in the light gaseous product fraction which must undergo more expensive gaseous product processing steps to recover commercially acceptable grades of light olefin products. A preferred quench medium is selected from the group consisting of water and streams that are substantially water. More preferably, the quench medium is a stream which is substantially water and is selected from the several fractions of the heavy product fraction from the quench tower.

The amount of quench medium circulated in the quench tower at a particular temperature for product quenching should be not more than what is needed to produce a heavy product fraction exiting the quench tower having a temperature at least about 5° C. higher than the first temperature of the oxygenate feedstock from the storage tank. In another embodiment, as already discussed, the oxygenate conversion reactor effluent stream is used directly as a heat exchanger fluid to provide heat to the oxygenate feedstock before it enters the oxygenate conversion reactor to contact the oxygenate conversion catalyst.

Preferably, the pressure in the quench tower and the temperature of the heavy product fraction effluent are maintained at effective levels for recovery of the highest quantity and quality of process heat. More preferably, the difference between the heavy product fraction effluent pressure and the pressure at which the feedstock is vaporized is below about 345 kPa, more preferably below about 207 kPa. The temperature of the heavy product fraction effluent from the quench tower preferably is maintained at no less than about 30° C. below the bubble point of the heavy product fraction effluent. Maintaining a temperature differential between the heavy product fraction effluent and its bubble point provides the highest possible bottoms temperature in the quench tower and the most economically practical recovery of useful heat from the heavy product fraction effluent.

Preferably, the heavy product fraction effluent (heavy product fraction) from the quench tower is pressurized and used for providing heat to other streams. In one embodiment, the heavy product fraction, or any, or all of the several fractions into which the heavy product fraction is divided, or streams from quench medium separations thereof, are used directly as a heat exchanger fluid to increase the heat content and/or temperature of the oxygenate feedstock at one or more of the stages with successively higher heat contents. Further, any of the several fractions or streams produced from the quench medium separations thereof may be used to increase the heat contents of other streams within the overall oxygenate conversion reaction and product recovery process. The cooled quench medium recovered from such fractions and streams may be returned back to the quench tower.

In a preferred embodiment, particularly when the oxygenate conversion is not complete and the quench medium consists essentially of water, the heavy product fraction is divided into two fractions, a first fraction and a second fraction. The relative quantities of the first fraction and the second fraction depend on the overall amount of heat that needs to be removed from the product effluent stream in the quench operation, and the temperature of the quench medium introduced into the quench tower. The relative quantities are set to optimize equipment cost for heat recovery and utility consumptions. The first fraction is cooled to a desired temperature and sent back to the quench tower as a recycle, i.e. quench water. The utility required to cool the first fraction, e.g. cooling water, may be reduced by using the product effluent stream from the oxygenate conversion reactor as a heat exchange fluid to heat the oxygenate feedstock before the feedstock enters the oxygenate conversion reactor and/or before the product effluent stream enters the quench tower.

The second fraction of the heavy product fraction effluent is sent to a fractionator to separate the quench medium, which consists essentially of water—a part of it may originate as the recycled portion of the byproduct water from the oxygenate conversion reaction when the feedstock oxygenate has at least one oxygen—from other compounds, such as unreacted oxygenates or certain heavier hydrocarbons from the oxygenate conversion reaction, present in the fraction. If other streams having compositions similar to or compatible with the second fraction exist within the oxygenate conversion and the associated product recovery process, such other streams are combined with the second fraction first and the combined stream is sent to the fractionator.

Generally it is desirable to fractionate a mixture into components as sharply as possible. In the present invention, it is preferable for the overhead oxygenate fraction and/or the heavies-containing fraction from the fractionator to have a composition of water as introduced in the second fraction of the heavy product fraction in the range of from about 15 mol % to about 99.5 mol %, preferably from about 25 mol % to about 90 mol %. An increase in the water composition of the overhead fraction tends to increase the condensation temperature, and more heat can be recovered economically from the overhead fraction of the fractionator to improve heat integration for the entire process. Preferably, the recovered overhead oxygenate fraction contains at least about 90 mol % of the oxygenate contained in the second fraction of the heavy fraction. More preferably, the recovered overhead oxygenate fraction contains at least about 99 mol % of the oxygenate contained in the second fraction of the heavy fraction.

The overhead fraction of the fractionator is condensed in a heat exchanger, i.e. a condenser, against the oxygenate feedstock at one of the stages, from one to about three where the oxygenate feedstock is given successively higher heat contents. It s preferable for the overhead fraction of the fractionator to have a pressure at least about 69 kPa higher than the pressure of the oxygen feedstock in the condensor. This pressure differential also increases the condensation temperature of the overhead fraction, making heat recovery from the overhead fraction more economical.

The bottoms fraction of the fractionator consists essentially of byproduct water from the oxygenate conversion reaction. Preferably, this bottoms fraction is pressurized and used to heat the oxygenate feedstock at one of the stages, from one to about three, where the oxygenate feedstock is given successively higher heat contents prior to entering the oxygenate conversion reactor. The fractionator is operated such that the temperature of the bottoms fraction is at least about 5° C., preferably at least about 25° C., higher than the first temperature of the oxygenate feed from storage. The operating temperature inside of the fractionator is determined by a number of parameters, including, but not necessarily limited to the fractionator overhead pressure and the overall pressure drop inside of the fractionator.

FIG. 1 shows one embodiment of a process flow diagram according to the invention to increase heat recovery and to improve heat integration. Liquid oxygenate feed 1, such as methanol, having a first heat content, at a first temperature and a first pressure, is heated by stream 35 in heat exchanger 2. Stream 35 is fractionator bottoms stream 33 from fractionator 24, which is pressurized by pump 34. The result is a first heated oxygenate feed stream 3 with a higher heat content than that of liquid oxygenate feed stream 1. First heated oxygenate feed stream 3 then is heated in another heat exchanger 4 by overhead fraction 26 from fractionator 24 to form a second heated oxygenate feed stream 5 with a higher heat content than that of stream 3. Heat exchanger 4 is a condensor or a partial condensor for fractionator 24. Second heated oxygenate feed stream 5 goes through steam pre-heater 6 to form a third heated oxygenate feed stream 7 which is further heated by oxygenate conversion product effluent 11 in heat exchanger 8 to form a fourth heated oxygenate feed stream 9 under the effective conditions—temperature, pressure, and proportion of liquid and vapor—desired for the conversion of the oxygenate feed. Oxygenate conversion product 11 is the effluent of oxygenate conversion reactor 10, after being separated from the deactivated oxygenate conversion catalyst which has carbonaceous deposits. Alternatively, heat exchanger 8 may comprise of a plurality of coils inside of oxygenate conversion reactor 10.

Fourth heated oxygenate feed stream 9 is fed to oxygenate conversion reactor 10 which contains catalyst suitable for converting the oxygenate feed to olefins. Oxygenate conversion reactor 10 may adopt various configurations—fixed bed, fluidized bed, riser, moving bed, or a combination thereof, with or without continuous catalyst regeneration. A fixed bed reactor normally is not favored due to the difficulty of withdrawing deactivated catalyst for regeneration and returning the regenerated catalyst back to the reactor. The oxygenate feed is converted to a product comprising light olefins and the catalyst becomes deactivated or partially deactivated by accumulating carbonaceous deposits which are formed as byproducts of the oxygenate conversion reaction.

Oxygenate conversion product effluent 11 flows through heat exchanger 8 and becomes cooled oxygenate conversion product effluent stream 12 which is sent to quench tower 13. Alternately, heat exchanger 8 may be eliminated and oxygenate conversion product effluent 11 is sent directly to quench tower 13 without intermediate cooling. In quench tower 13 oxygenate conversion product stream 12 contacts directly with a quench medium consisting essentially of water at an initial temperature over a series of suitable contacting devices. The amount of the quench medium needed in quench tower 13 is dictated by a number of factors, including, but not necessarily limited to the composition of the quench medium, the temperature of quench medium recycle introduced to quench tower 13, and desired temperature differences and pressure differences between various streams. These differences are discussed where appropriate. The gaseous products are separated as light product fraction stream 14. Heavy product fraction stream 15, which exits from the bottom of the quench tower at an exiting temperature, comprises the bulk of byproduct water, a portion of the unreacted oxygenate feedstock (except those oxygenates that are gaseous under the quenching conditions), a small portion of the oxygenate conversion byproducts, particularly heavy hydrocarbons (C5+), and usually the bulk of the quench medium.

A preferred quench medium is water, which is for all intents and purposes indistinguishable from byproduct water. This eliminates the need for steps to separate the quench medium from byproduct water in the heavy product fraction. In the event that a quench material other than water is used and this quench material is substantially in a liquid form under quenching conditions, heavy product fraction 15, or any, or all of the several fraction into which the heavy product fraction is divided may be processed to separate the quench medium from byproduct water. For example, if the quench medium is a high boiling hydrocarbon such as diesel fuel or similar streams, it is immiscible with byproduct water. Such a quench medium can be separated by a properly designed weir system in the bottom of quench tower 13, or in an API separator or other similar devices at many different points of the process in the present invention. Further, if any heavy hydrocarbons (C5+) are formed in the oxygenate conversion reaction, they also may be removed from byproduct water in stream 15 or other points in the process in substantially the same manner as or along with the removal of the quench medium. If the quench medium is a relatively light material which is substantially gaseous under the quenching conditions, and hence being present in substantial quantities in the light product fraction, such a quench medium can be separated in downstream olefin recovery processes encompassing the entire oxygenate conversion and olefin recovery and purification process.

Regardless, the exiting pressure of heavy product fraction stream 15 should be less than about $345 \times 10^3$ pascals (345 kPa) below the pressure of liquid oxygenate feed 1. Preferably, the exiting temperature of heavy product fraction stream 15 is maintained at no less than about 25° C. below the bubble point of byproduct water in stream 15. A preferred pressure difference between heavy product fraction stream 15 (lower pressure) and liquid oxygenate feed 1 (higher pressure) is less than 207 kPa.

Heavy product fraction stream (quench tower bottoms stream) 15 may be used to provide heat to the oxygenate feedstock in heat exchangers 2, 4, and/or 6 to increase the heat content of the feedstock. The oxygenate feedstock contains successively higher heat contents at these stages. One or more of these stages also may be eliminated. Preferably, quench tower bottoms stream 15 is divided into two fractions, recycle fraction 18 and fractionator feed fraction 21. Recycle fraction 18, a quench water recycle stream, is cooled in exchanger 19 and recycled as quenching stream 20 back to quench tower 13. Alternatively, recycle fraction 18 or 20 may be split further into several fractions and these fractions may be cooled to different temperatures in different heat exchangers. These fractions, or some of them, at different temperatures may be introduced into quench tower 13 at different points to better integrate heat recovery and minimize utility consumption. The heat content of fraction 18 may be used to provide heat to the oxygenate feedstock in the heat exchanger 2, 4, and/or 6, or at different locations of the entire oxygenate conversion and olefin recovery and purification process to provide heat and to increase heat recovery.

Fractionator feed fraction 21, optionally mixed with other water containing streams 22, is sent to fractionator 24. At least two streams, fractionator overhead stream 26 and fractionator bottoms stream 33, are fractionated from fractionator feed fraction 21. Fractionator overhead stream 26 should contain at least about 15 mol %, preferably at least about 25 mol %, of water from the oxygenate conversion reaction. Conjunctively with or alternatively to this composition preference, the temperature of fractionator overhead stream 26 should be at least about 10° C. higher than the boiling temperature of the oxygenate feed under the conditions of heat exchanger 4.

Sufficient heat is added to fractionator 24 via reboiler 25, which when coupled with a sufficient number of trays in fractionator 24 results in producing fractionator bottoms stream 33 which comprises substantially all byproduct water and quench medium introduced with stream 23.

Preferably, the quench medium is water. When water is used as the quench medium, bottoms stream 33 consists essentially of the bulk of byproduct water from the oxygenate conversion reaction and no further steps are necessary to separate byproduct water from the quench medium. If the quench medium is a material other than water and has not previously been separated from byproduct water prior to introduction into the quench tower, this quench material may be separated from byproduct water in bottoms stream 33, or later in the process as described above. Further, if any heavy hydrocarbons (C5+) are formed in the oxygenate conversion process, they also may be removed from byproduct water in stream 33, or later in the process in substantially the same manner as or along with the removal of the quench medium.

Fractionator bottoms stream 33, before leaving fractionator 24, is at a temperature which is at least about 5° C., preferably at least about 25° C., higher than the first temperature of the oxygenate feed introduced from storage 1 to heat exchanger 2. The pressure at the top of fractionator 24 should be at least 69 kPa higher than the pressure in heat exchanger 4 to increase heat recovery. Stream 35 is used to heat up liquid oxygenate feedstock 1 in heat exchanger 2. For better heat recovery, exiting stream 36 from heat exchanger 2 preferably has a temperature equal to or less than about the temperature of stream 21.

One way to further improve heat integration and to increase heat recovery is to use fractionator overhead stream 26 as the heat source for heat exchanger 4. The cooled fractionator overhead stream 27 may be fractionated further in separator 28 into vapor discharge stream 29 and liquid reflux 30 which is sent back to fractionator 24 after pressure adjustment with pump 31. It is important to maintain cooled fractionator overhead stream 27 at a temperature above the boiling point of the first heated oxygenate feed 3 to provide favorable heat transfer.

The invention will be better understood with reference to the following example, which illustrate, but should not be construed as limiting the present invention.

EXAMPLE I

A liquid methanol feed 1 at about 386.1 kPa pressure and 38° C. absorbs heat to increase its heat content in heat exchanger 2 from stream 35, at 158° C. and 1,276 kPa pressure, from methanol/water fractionator 24 to form the first heated methanol feed stream 3 at a temperature of about 100° C. and a pressure of 351.6 kPa. The first heated methanol feed stream 3 with 4,722 kJ/mole heat content absorbs heat from the fractionator overhead stream 26 in the heat exchanger 4 to form the second heated methanol feed stream 5 with a heat content of 6,521 kJ/mole. Stream 5 is heated further by steam in heat exchanger 6 to form the third heated methanol feed stream 7 which has even higher heat content than the third heated methanol feed stream 7—7,390 kJ/mole. The third heated methanol feed stream 7 is heated in heat exchanger 8 to form the fourth heated methanol feed stream 9 with the methanol conversion product effluent 11 from the oxygenate conversion reactor 10. The fourth heated methanol feed stream 9, having a much higher heat content of 17,102 kJ/mole, is suitable for contacting a catalyst in the oxygenate conversion reactor 10 to form a deactivated oxygenate conversion catalyst having carbonaceous deposits and a product 11 comprising olefins, particularly light olefins. The oxygenate conversion reactor 10 is a fluidized bed reactor with continuous catalyst regeneration and recirculation (not shown). The oxygenate conversion product 11 is separated from deactivated oxygenate conversion catalyst having carbonaceous deposits and used to heat the stream 9 and form a cooled methanol conversion product stream 12. A part of the deactivated catalyst is withdrawn and removed for regeneration (not shown). It is preferable to remove at least about 1.0 wt % of the carbonaceous deposits from the deactivated catalyst during the regeneration. It is also preferred to remove less than about 98.0 wt % of the carbonaceous deposits from the deactivated catalyst during regeneration. The regenerated catalyst is recycled back into the oxygenate conversion reactor 10 for contacting the oxygenate feed. 99.8wt % of the methanol in stream 9 is converted in the reactor 10, with the unconverted balance exiting in the stream 11.

The cooled methanol conversion product stream 12 exiting the heat exchanger 8 is sent to the quench tower 13, contacting directly a quench medium consisting essentially of water. The quench tower 13 is equipped with suitable contacting devices inside. Most hydrocarbon products are separated as a gaseous product stream 14. Heavier products, water, and unreacted methanol are discharge from the quench tower 13 as the quench tower bottoms stream 15 at a temperature of about 116° C. and a pressure of about 262 kPa. The quench tower bottoms stream 15 is pressurized by the pump 16 to form the pressurized quench tower bottoms stream 17 at about 689.5 kPa. About 83 mol % of the pressurized quench tower bottoms stream 17 forms the recycle fraction 18 and is sent through the cooling exchanger 19 to form the quenching stream 20 at a lower temperature. The quenching stream 20 is returned to the quench tower 13.

The rest of the pressurized quench tower bottoms stream 17, about 17 mol % becomes the fractionator feed fraction 21. The fractionator feed fraction 21 is combined with another methanol/water stream 22, a small stream recovered from other sources within the overall oxygenate conversion and product recovery process. The combined stream 23 is sent to the fractionator 24. The fractionator overhead stream 26 containing about 89 mol % water and about 10.5 mol % of methanol at a temperature of 152° C. and a pressure at 551.6 kPa is sent to the heat exchanger 4. The bottoms from fractionator 24 is heated with steam in the heat exchanger 25 to produce the fractionator bottoms stream 33 at 158° C. and about 585.4 kPa, which contains primarily water with only traces of other components. The fractionator bottoms stream 33 is pressurized to about 1274.8 kPa and the resulting stream 35 is used for the heat exchanger 2 to heat the liquid methanol feed 1. After heat exchange, the byproduct warm water stream 36 has a temperature of 46° C. at a pressure of 861.2 kPa.

Table 1 shows the product selectivity and the composition of product stream 11 of methanol conversion used for obtaining the results shown in Table 2 and Table 3. The feed rates, compositions, pressures, and temperatures of various streams as described in Example I are shown in Table 2. The duties of key exchangers 2, 4, and 25 are tabulated in Table 3.

TABLE 1

| Component | Product Selectivity (wt %) | Hydrocarbon Composition in Stream 11 (mol %) |
| --- | --- | --- |
| Hydrogen | 0.15 | 0.73 |
| Carbon Monoxide | 0.03 | 0.01 |
| Carbon Dioxide | 0.12 | 0.03 |
| Methane | 1.00 | 0.61 |
| Ethylene | 40.90 | 14.40 |
| Ethane | 0.83 | 0.27 |
| Propylene | 40.90 | 9.60 |
| Propane | 0.21 | 0.05 |
| Butenes | 8.89 | 1.56 |
| Butanes | 0.09 | 0.02 |
| Pentenes | 3.95 | 0.56 |
| Pentanes | 0.04 | 0.01 |
| Coke | 2.89 | — |
| Total | 100.00 | 27.84 |

TABLE 2*

| Stream No. | Rate (mol/h) | Methanol (mol %) | Water (mol %) | Pressure (kPa) | Temperature (° C.) | Heat Content (kJ/mol) |
| --- | --- | --- | --- | --- | --- | --- |
| 1 | 10,000.0 | 98.23 | 1.77 | 386.1 | 35.2 | 582 |
| 3 | 10,000.0 | 98.23 | 1.77 | 351.6 | 100.1 | 4,722 |
| 5 | 10,000.0 | 98.23 | 1.77 | 330.9 | 98.2 | 6,521 |
| 7 | 10,000.0 | 98.23 | 1.77 | 317.2 | 96.9 | 7,390 |
| 9 | 10,000.0 | 98.23 | 1.77 | 317.2 | 96.9 | 17,102 |
| 11 | 13,918.9 | 0.14 | 72.02 | 275.8 | 407.9 | 25,424 |
| 12 | 13,918.9 | 0.14 | 72.02 | 262.0 | 124.9 | 18,475 |
| 14 | 3,946.7 | 0.04 | 1.78 | 241.3 | 37.8 | 6,841 |
| 15 | 92,909.4 | 0.18 | 99.82 | 262.0 | 115.6 | 3,856 |
| 21 | 9,972.2 | 0.18 | 99.82 | 689.5 | 115.6 | 3,859 |
| 22 | 863.8 | 0.21 | 99.78 | 689.5 | 43.4 | 1,394 |
| 26 | 1,118.0 | 10.54 | 89.42 | 551.6 | 151.9 | 21,740 |
| 27 | 1,118.0 | 10.54 | 89.42 | 517.1 | 138.8 | 5,566 |
| 29 | 53.9 | 36.42 | 62.75 | 517.1 | 138.8 | 886 |
| 33 | 10,782.2 | trace | 100.00 | 585.4 | 157.9 | 5,302 |
| 35 | 10,782.2 | trace | 100.00 | 1,274.8 | 158.1 | 5,310 |
| 36 | 10,782.2 | trace | 100.00 | 861.2 | 46.1 | 1,476 |

TABLE 3*

| Exchanger No. | Duty (10⁶ kJ/h) |
| --- | --- |
| 2 | 41.4 |
| 4 | 18.9 |
| 6 | 8.6 |
| 8 | 97.1 |
| 19 | 191.7 |
| 25 | 38.1 |

*As compiled using the Simulation Sciences, Inc. PRO/II chemical process simulation program, utilizing the Modified Panagiotopoulos-Reid modifications to the Soave-Redlich-Kwong equation of state.

*As complied using the Simulation Sciences, Inc. Pro/II chemical process simulation program, utilizing the Modified Panagiotopoulos-Reid modifications to the Soave-Redlich-Kwong equation of state.

The results show that in the oxygenate conversion process, the external heat needed to bring the oxygenate feedstock to conditions desirable for contacting the catalyst, represented in the preferred embodiment by heat exchanger 6, is reduced as a result of increased heat recovery and improved heat integration of the process.

Persons of ordinary skill in the art will recognize that many modifications may be made to the present invention without departing from the spirit and scope of the present invention. The embodiment described herein is meant to be illustrative only and should not be taken as limiting the invention, which is defined by the following claims.

We claim:

1. A process for converting an oxygenate to olefins with increased heat recovery and heat integration, said process comprising:

heating a feedstock comprising said oxygenate having a first heat content from a first temperature to a second temperature through from one to about three stages having successively higher heat contents;

contacting said feedstock at said second temperature with a catalyst comprising a molecular sieve under conditions effective to produce a deactivated catalyst having carbonaceous deposits and a product comprising said olefins, wherein said molecular sieve comprises pores having a diameter smaller than about 10 Angstroms and said product has a third temperature which is higher than said second temperature;

separating said deactivated catalyst from said product;

quenching said product with a medium at an initial temperature and in an amount sufficient for forming a light product fraction and a heavy product fraction wherein said light product fraction comprises light olefins and said heavy product fraction has a final temperature which is higher than said first temperature by at least about 5° C.; and using said heavy product fraction to provide heat at one or more of said stages to achieve said higher heat contents.

2. A process for converting an oxygenate to olefins with increased heat recovery and heat integration, said process comprising:

heating a feedstock comprising said oxygenate having a first heat content and a first pressure from a first temperature to a second temperature through from one to about three stages having successively higher heat contents;

contacting said feedstock at said second temperature with a catalyst comprising a molecular sieve under conditions effective to produce a deactivated catalyst having carbonaceous deposits and a product comprising said olefins, wherein said molecular sieve comprises pores having a diameter smaller than about 5 Angstroms and said product has a third temperature which is higher than said second temperature;

separating said deactivated from said product;

quenching said product with a mixture at an initial temperature and in an amount sufficient for forming a light product fraction and a heavy product fraction, wherein said mixture consists essentially of water, said light product fraction comprises light olefins, said heavy product fraction comprises water and unreacted feedstock and said heavy product fraction has a final temperature which is higher than said first temperature by at least about 5° C.;

dividing said heavy product fraction into a first fraction and a second fraction;

cooling said first fraction to said initial temperature;

recycling said first fraction at said initial temperature to become part of said mixture for said quenching;

fractionating said second fraction into a third fraction and a fourth fraction wherein said third fraction consists essentially of water, and said fourth fraction comprises at least about 15 mol % of water;

heating and pressurizing said third fraction to a fourth temperature and second pressure wherein said fourth temperature is at least about 10° C. higher than said first temperature and said second pressure is higher than said first pressure; and using said third fraction to heat said feedstock at one of said stages, thereby forming a stream having a second heat content which is higher than said first heat content.

3. The process of claim 1 wherein said diameter is smaller than about 5 Angstroms.

4. The process of claim 1 wherein said molecular sieve comprises a silicoaluminophosphate (SAPO).

5. The process of claim 1 wherein said molecular sieve comprises a SAPO selected from the group consisting of SAPO-17, SAPO-18, SAPO-34, SAPO-44, and mixtures thereof.

6. The process of claim 1 wherein said molecular sieve comprises a zeolite.

7. The process of claim 1 wherein said molecular sieve comprises a zeolite selected from the group consisting of ZSM-5, ZSM-34, chabazite, erionite, offretite, and mixtures thereof.

8. The process of claim 1 wherein said medium consists essentially of water.

9. The process of claim 1 further comprising:

withdrawing a part of said deactivated catalyst after said separating from said product;

removing at least 1.0 wt % of said carbonaceous deposits from said part of said deactivated catalyst to form a regenerated catalyst; and recycling said regenerated catalyst for said contacting with said feedstock.

10. The process of claim 1 wherein said oxygenate is selected from the group consisting of methanol, dimethyl ether, ethanol, methyl ethyl ether, dimethyl carbonate, methyl formate, methyl acetate, diethyl ether, and mixtures thereof.

11. The process of claim 1 wherein said oxygenate is selected from the group consisting of methanol, dimethyl ether, dimethyl carbonate, and mixtures thereof.

12. The process of claim 1 wherein said molecular sieve comprises a MeAPSO selected from the group consisting of SrAPSO-34, NiAPSO-34, CoAPSO-34, MnAPSO-34, SrAPSO-18, SrAPSO-17, NiAPSO-17, CoAPSO-17, MnAPSO-17 and mixtures thereof.

13. The process of claim 1 wherein said feedstock further comprises a diluent selected from the group consisting of water, carbon dioxide, carbon monoxide, nitrogen, hydrogen, argon, helium, methane, ethane, and mixtures thereof.

14. The process of claim 1 wherein said molecular sieve comprises SAPO-34.

15. The process of claim 1 wherein said oxygenate is selected from the group consisting of methanol, dimethyl ether, and mixtures thereof and said molecular sieve comprises SAPO-34.

16. The process of claim 2 wherein said fourth fraction comprises at least about 25 mol % of water.

17. The process of claim 2 further comprising:

withdrawing a part of said deactivated catalyst after said separating from said product;

removing at least 1.0 wt % of said carbonaceous deposits from said part of said deactivated catalyst to form a regenerated catalyst; and recycling said regenerated catalyst for said contacting with said feedstock.

18. The process of claim 2 wherein said fourth temperature is at least about 25° C. higher than said first temperature.

19. The process of claim 2 wherein said molecular sieve is selected from the group consisting of SAPO-17, SAPO-18, SAPO-34, SAPO-44, and mixtures thereof.

20. The process of claim 2 wherein a portion of said first fraction is used to provide heat for one or more of said stages to achieve said higher heat contents.

21. The process of claim 1 wherein said feedstock is maintained at a first pressure prior to said heating and said heavy product fraction has a second pressure, and wherein said second pressure is lower than said first pressure by no more than about 345 kPa.

22. The process of claim 1 wherein said feedstock is maintained at a first pressure prior to said heating and said heavy product fraction has a second pressure, and wherein said second pressure is lower than said first pressure by no more than about 207 kPa.

23. A process for converting an oxygenate to light olefins comprising:

heating a feedstock comprising said oxygenate having a first heat content and a first pressure from a first temperature to a second temperature through from one to about three stages having successively higher heat contents wherein said oxygenate is selected from the group consisting of methanol, dimethyl ether, methyl formate, dimethyl carbonate, and mixtures thereof;

contacting said feedstock at said second temperature with a catalyst comprising a small pore non-zeolitic molecular sieve under conditions effective to produce a deactivated catalyst having carbonaceous deposits and a product comprising said light olefins, and said product has a third temperature which is higher than said second temperature;

separating said deactivated catalyst from said product;

quenching said product with a mixture consisting essentially of water at an initial temperature and in an amount sufficient for cooling said product and separating said light olefins from a heavy product fraction wherein said heavy product fraction comprises said water, heavier products from said converting and unconverted oxygenate, said heavy product fraction has a final temperature higher than said initial temperature, and said final temperature is higher than said first temperature by at least about 5° C.;

dividing said heavy product fraction into a first fraction and a second fraction;

cooling said first fraction to said initial temperature;

recycling said cooled first fraction at said initial temperature to become part of said mixture for said quenching;

fractionating said second fraction into a third fraction and a fourth fraction wherein said third fraction consists essentially of water, and said fourth fraction comprises at least about 15 mol % of water, heating and pressurizing said third fraction to a fourth temperature and a second pressure wherein said fourth temperature is at least about 10° C. higher than said first temperature and said second pressure is higher than said first pressure; and using said third fraction to heat said feedstock at one of said stages, thereby forming a stream having a second heat content which is higher than said first heat content.

24. The process of claim 23 wherein said feedstock further comprises a diluent selected from the group consisting of nitrogen, water, hydrogen, carbon dioxide, carbon monoxide, argon, helium, methane, ethane, and mixtures thereof.

25. The process of claim 23 wherein said fifth fraction comprises at least about 25 mol % of said water and said fourth temperature is at least about 25° C. higher than said first temperature.

26. The process of claim 23 wherein said small pore non-zeolitic molecular sieve is selected from the group consisting of SAPO-17, SAPO-18, SAPO-34, SAPO-44, and mixtures thereof.

27. A process for converting methanol to light olefins comprising:

heating a feedstock comprising said methanol having a first pressure and a first heat content from a first temperature to a second temperature through from one to about three stages having successfully higher heat contents;

contacting said feedstock at said second temperature with a catalyst comprising SAPO-34 under conditions effective to produce a deactivated catalyst having carbonaceous deposits and a product comprising said light olefins, and said product has a third temperature which is higher than said second temperature;

separating said deactivated catalyst from said product;

withdrawing a part of said deactivated catalyst after said separating from said product;

removing at least 1.0 wt % of said carbonaceous deposits from said part of said deactivated catalyst to form a regenerated catalyst;

recycling said regenerated catalyst for said contacting with said feedstock;

quenching said product with a medium consisting essentially of water at an initial temperature in an amount sufficient for cooling said product thereby separating said light olefins from a heavy product fraction wherein said heavy product fraction comprises water, heavier products from said converting, and unconverted oxygenates, and said heavy product fraction has a final temperature which is higher than said first temperature by at least about 5° C.;

separating a portion of said heavy product fraction after said quenching;

dividing said portion into a first fraction and a second fraction;

cooling said first fraction to said initial temperature;

recycling said cooled first fraction back to quench said product;

fractionating said second fraction into a third fraction and a fourth fraction wherein said third fraction consists essentially of water, and said fourth fraction comprises at least about 15 mol % of water;

heating and pressurizing said third fraction to a fourth temperature and a second pressure wherein said fourth temperature is at least about 25° C. higher than said first temperature and said second pressure is at least 69 kPa higher than said first pressure; and using said third fraction to provide heat at one or more of said stages to achieve said higher heat contents.

* * * * *